United States Patent [19]

Barcel

[11] Patent Number: 5,275,171
[45] Date of Patent: Jan. 4, 1994

[54] IMPLANTABLE LEAD AND SENSOR

[75] Inventor: James E. Barcel, Simi Valley, Calif.

[73] Assignee: Siemens Pacesetter, Inc., Sylmar, Calif.

[21] Appl. No.: 562,771

[22] Filed: Aug. 6, 1990

[51] Int. Cl.$^5$ .............................................. A61N 1/05
[52] U.S. Cl. ................................................... 607/122
[58] Field of Search ............. 128/642, 784, 786, 419 P

[56] References Cited

U.S. PATENT DOCUMENTS

| | | | |
|---|---|---|---|
| 4,202,339 | 5/1980 | Wirtzfeld et al. | 128/419 PG |
| 4,399,820 | 8/1983 | Wirtzfeld et al. | 128/419 PG |
| 4,750,495 | 6/1988 | Moore et al. | 128/419 PG |
| 4,791,935 | 12/1988 | Baudino et al. | 128/637 |
| 4,815,469 | 3/1989 | Cohen et al. | 128/634 |

OTHER PUBLICATIONS

*A Practical Guide to Cardiac Pacing*, Moses et al., pp. 32-35, Little, Brown & Co., Boston/Toronto 1983.

Primary Examiner—William E. Kamm
Assistant Examiner—Scott M. Getzow
Attorney, Agent, or Firm—Leslie S. Miller; Lisa P. Weinberg

[57] ABSTRACT

A physiological sensor forms an integral part of an implantable stimulation/sensing lead used with a medical device, such as a pacemaker. The stimulation/sensing lead includes a tip electrode to which a distal end of a first conductor is connected. The sensor is inserted in series with respective portions of a second conductor. A distal end of the second conductor/sensor is connected to the tip electrode. Operation of the stimulation/sensing lead occurs unipolarly through the first conductor only, with a signal return path being provided through the tip electrode and conductive body fluids. The sensor does not form part of the electrical circuit to the tip electrode, and there are no electrical connections or breaks in the insulation along the entire length of the first conductor. Electrical contact with the sensor is achieved during a time window when the stimulation/sensing lead is not being used by applying an appropriate operating signal, and measuring the resultant output signal, at the proximal ends of the first and second leads.

19 Claims, 2 Drawing Sheets

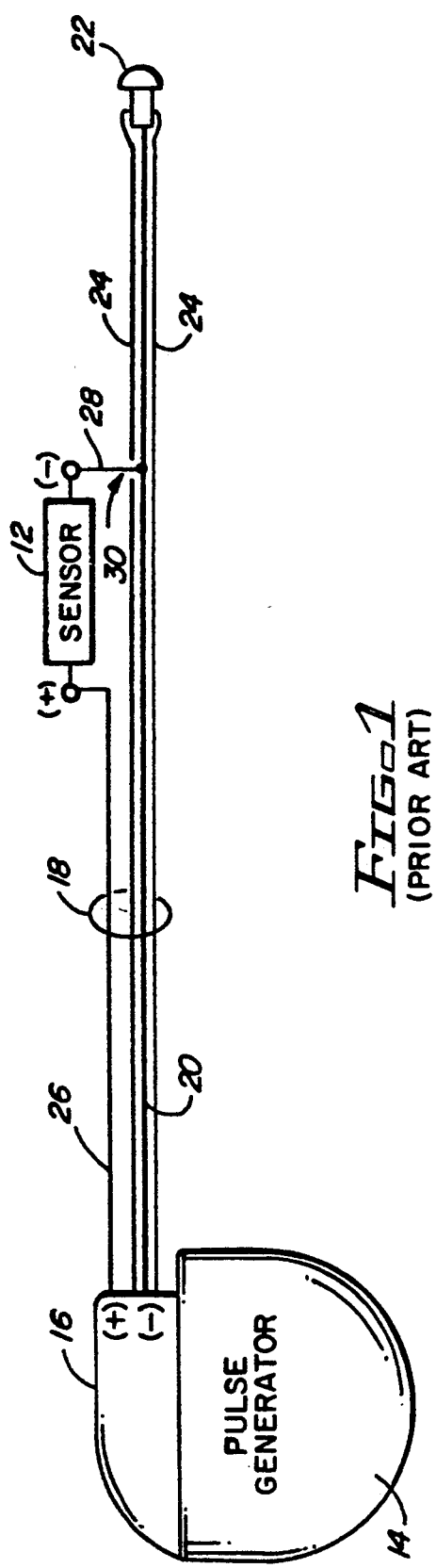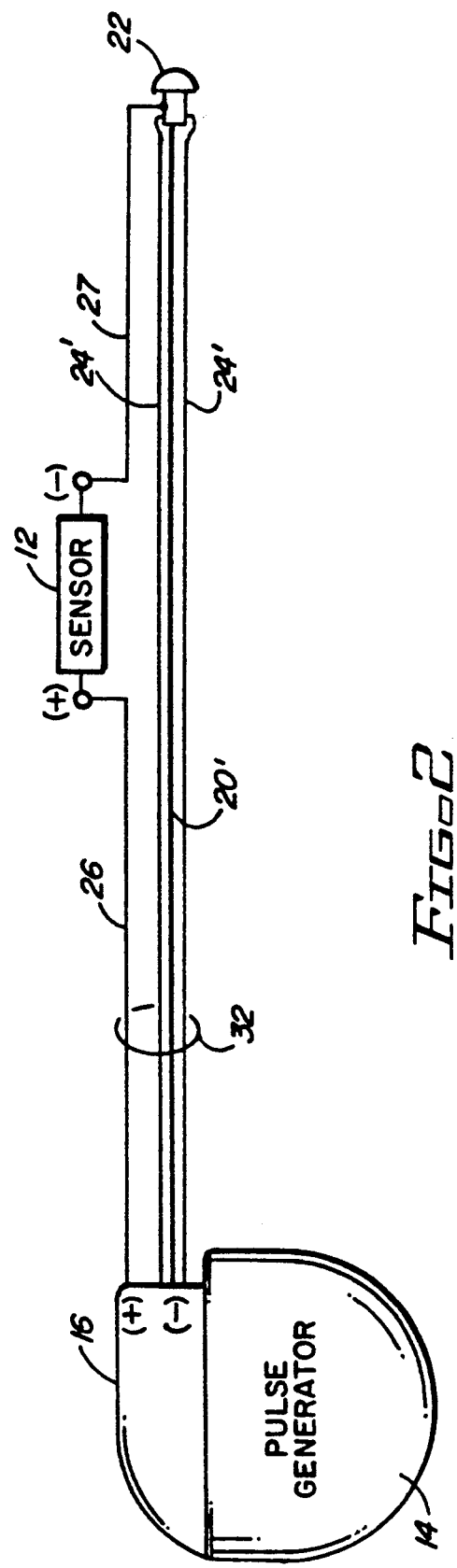

IMPLANTABLE LEAD AND SENSOR

BACKGROUND OF THE INVENTION

The present invention relates to implantable leads designed for use with medical devices, and more particularly to implantable leads having a physiological sensor as an integral part thereof.

In recent years, significant advances have been made in the medical arts relative to the use of implantable or transportable medical devices that measure, regulate, and/or control various body functions or organs of a patient. Many of these devices require one or more electrical "leads" that couple the appropriate medical device, whether implanted within the patient or carried external (non-implanted) to the patient, to a desired tissue location.

Such leads typically include one or two elongate flexible electrical conductors insulated with a suitable electrical insulating material. At or near the end of the lead farthest from the medical device, termed the "distal" end, the electrical conductors are connected to one or more suitable electrodes. These electrodes are specially designed for contacting and interfacing with appropriate body tissue. The electrodes (commonly referred to as "tip" or "distal" electrodes) may include a small or large surface area, depending upon the function they are to perform. At the end of the lead closest to the medical device, termed the "proximal" end, the electrical conductors are connected to a suitable electrical connector, which connector is specially designed for detachable connection to the medical device.

All components used in such implantable leads are, of course, made only from body compatible materials, thereby allowing the leads to be freely used within the patient's body.

While the function performed by implantable leads is simply that of an insulated electrical conductor, their construction and design is much more complicated. See, e.g., Moses et al., *A Practical Guide to Cardiac Pacing*, pp. 32-35 (Little, Brown & Co., Boston/Toronto 1983). For example, where the lead is positioned in or near the heart, or other moving body organs or tissue, the lead must be resistant to fracture in order to withstand constant flexure. (Consider, e.g., that the typical heart beats about 40 million times per year.) Hence, the wire used for the lead conductor must be made of a metal alloy that allows good conductivity, is fatigue resistant, is coiled to increase flexibility, and is frequently multifilar to provide electrical redundancy within the lead. Further, as has been mentioned, the conductors (wires) used in the lead must be insulated, typically with Silastic or polyurethane, so that only the metal tip or electrode is exposed.

It is known in the art to incorporate an implantable sensor as an integral part of an implantable pacemaker lead, as described, for example, in U.S. Pat. Nos. 4,750,495 and 4,791,935. Generally, the sensors described in these patents are oxygen sensors used to optically detect the amount of oxygen in the blood. Optical detection is accomplished by incorporating a light emitting diode (LED) and a phototransistor in the sensor. The LED emits radiation of a prescribed frequency that is directed through a suitable lens or window to the blood. The amount of such radiation reflected back through the window to the phototransistor is a function of the amount of saturated oxygen in the blood. Hence, by monitoring the output signal from the phototransistor, it is possible to determine how much oxygen is present in the blood. This determination, in turn, is used to control or adjust the rate at which the pacemaker provides stimulation pulses on demand to the heart.

As shown in these patents, when a sensor is included as a part of the implantable lead, the conductors of the lead are utilized to make electrical contact with the sensor. Heretofore, this has required a breaking or puncturing of the insulation of the lead at the location where the sensor is to be positioned along the length of the lead, so that electrical contact can be made with the electrical conductors of the lead. Unfortunately, even though the area of such breakage or puncture may be very small, and even though the entire area of the insulation breakage or puncture is covered by an additional insulation sleeve, this process (of electrically connecting the sensor to the conductor within the lead) compromises the integrity of the insulation at the location where the electrical contact is made with the lead conductor. Further, because some means, e.g., crimping, welding, etc., must be used to make and maintain physical and electrical contact of a conductor from the sensor to the lead conductor, the lead conductor itself may be structurally weakened at the point of contact. Over a long period of time when the lead is immersed in a fluid environment and subjected to constant flexing and bending, such as when the lead is implanted in a patient, there may thus develop slight leaks in the insulation at the point of insulation breakage or puncture, or significant changes in conductivity of the conductor at the point of electrical contact with the sensor. Such changes may noticeably alter the overall impedance of the lead, and thus adversely impact operation of the pacemaker (or other medical device). What is needed, therefore, is a lead construction that allows a sensor, such as an optical oxygen sensor, to be embedded within a pacing (or other) implantable lead that does not compromise the integrity of the lead insulation nor the lead conductivity, thereby providing long term impedance stability of the lead in fluid environments, and further ensuring a continuous, uninterrupted conductor/insulation route along the entire length of the lead. The present invention advantageously addresses this and other needs.

SUMMARY OF THE INVENTION

In accordance With one aspect of the present invention, a physiological sensor forms an integral part of an implantable stimulation/sensing lead used with an implantable medical device, such as a pacemaker. The stimulation/sensing lead includes at least two conductors and a tip electrode to which a distal end of a first conductor is connected. The sensor is inserted in series with respective portions of a second conductor. That is, the second conductor is split into two portions by breaking or cutting it at a desired location along the lead length where the sensor is to be inserted. The two cut ends of the second conductor at the desired location are attached to respective terminals of the sensor. A distal end of the second conductor is connected to the tip electrode. Proximal ends of both the first and second conductors are detachably connected to the implantable medical device by means of a suitable electrical connector.

In accordance with another aspect of the invention, operation of the stimulation/sensing lead occurs unipolarly through the first conductor only, with a signal return path being provided through the tip electrode and conductive body fluids. Advantageously, the sensor does not form part of the electrical circuit to the tip electrode, and there are no electrical connections or breaks in the insulation along the entire length of the first conductor, thus assuring a continuous conductor/insulation route to the tip electrode through the first conductor. This configuration thus maximizes insulation distance between electrical contacts and provides long term impedance stability in body fluid environments.

In accordance with yet another aspect of the invention, electrical contact with the sensor is achieved during a time window when the stimulation/sensing lead is not being used by applying an appropriate operating signal, and measuring the resultant output signal, at the proximal ends of the first and second conductors of the implantable lead. A signal path to the sensor is provided through the proximal end of the second conductor and through the second conductor to a first sensor terminal. A signal return path from the sensor is provided from a second sensor terminal, through the remaining portion of the second conductor to the tip electrode, and from the tip electrode through the first conductor to the proximal end of the first conductor.

One embodiment of the present invention may thus be characterized as an implantable lead and sensor combination adapted for use with a medical device. Such lead and sensor combination includes a first conductor having a proximal end and a distal end, and first insulation means for electrically insulating the first conductor without interruption along its entire length. Further, the combination includes a tip electrode electrically connected to the distal end of the first conductor. There is also included a second conductor having a proximal end and a distal end. The distal end of the second conductor is also electrically connected to the tip electrode.

A sensor, having first and second terminals to which electrical contact must be made for its operation, also forms part of the combination. This sensor is electrically inserted in series with the second conductor at a location intermediate the proximal and distal ends of the second conductor. The proximal end of the second conductor is electrically connected to the first sensor terminal through a proximal portion of the second conductor. Similarly, the distal end of the second conductor is electrically connected to the second sensor terminal through a distal portion of the second conductor. Second insulation means are then used for electrically insulating the second conductor along its entire length, i.e., for electrically insulating the sensor as well as both the proximal and distal portions of the second conductor. The proximal ends of the first and second conductors are adapted for detachable electrical connection with the medical device.

Advantageously, such lead/sensor combination maintains electrical contact continuously and uninterruptedly with the tip electrode through the first conductor of the lead, thereby assuring impedance stability of the lead in fluid environments. Further, such lead/sensor combination allows electrical contact to be selectively made with the sensor through the proximal end of the first conductor and the proximal end of the second conductor. The first terminal of the sensor is electrically contacted through the proximal end of the second conductor. The second terminal of the sensor is electrically contacted through the proximal end of the first conductor by way of an electrical path through the first conductor to the tip electrode and through the distal end of the second conductor to the second sensor terminal.

It is thus a primary feature of the present invention to provide an implantable lead that includes an implantable sensor as an integral part thereof, and wherein the sensor is fully operable from a proximal end of the lead, but wherein the sensor does not interfere in any way with use of the implantable lead.

It is an additional feature of the present invention to provide such an implantable lead/sensor combination that maximizes the insulation distance between electrical contacts of the lead, thereby providing long term impedance stability in fluid environments.

It is another feature of the invention to provide such an implantable lead/sensor combination that ensures a continuous, uninterrupted, uncontacted, conductor/insulation signal path for the lead from a proximal connector to a distal electrode, where the proximal connector may be detachably secured to a suitable medical device, and the distal electrode may be positioned to contact desired body tissue.

It is yet a further feature of the invention to provide such an implantable lead/sensor combination that utilizes a conventional two-conductor (bipolar) coaxial lead body assembly, thereby facilitating the combination's assembly and manufacture.

Yet another feature of the invention provides a blood oxygen sensor as an integral part of an implantable pacemaker lead, with the oxygen sensor being fully operable from a proximal end of the lead, but without affecting in any way operation of the pacemaker lead, thereby enabling a rate responsive pacemaker to reliably measure the oxygen content of blood using such sensor, and then use the resulting measured value as a parameter to adjust the pacing rate of the pacemaker, with pacing pulses being provided to cardiac tissue through the pacemaker lead.

BRIEF DESCRIPTION OF THE DRAWINGS

The above and other aspects, features and advantages of the present invention will be more apparent from the following more particular description thereof, presented in conjunction with the following drawings wherein:

FIG. 1 is a schematic diagram illustrating the manner of using an in-lead sensor as taught in the prior art;

FIG. 2 is a schematic diagram illustrating the use of an in-lead sensor in accordance with the present invention;

DETAILED DESCRIPTION OF THE INVENTION

Figure 3A:
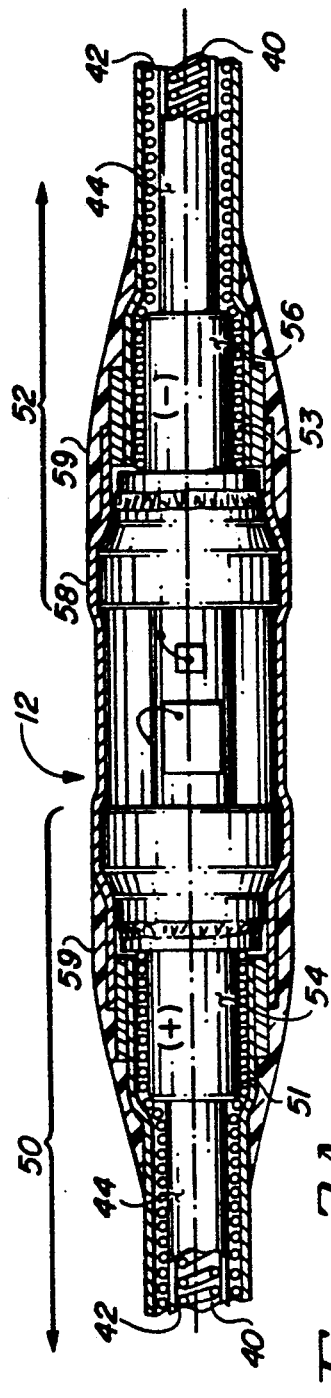
FIGS. 3A and 3B are sectional views of the sensor portion and the distal tip portion, respectively, of an implantable lead with integral sensor made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

Referring first to FIG. 1, there is shown a schematic diagram illustrating the manner of using an in-lead sensor 12 as taught in the prior art. The in-lead sensor 12 requires that a voltage potential be developed across respective terminals, identified by (+) and (−), of the sensor so that an appropriate signal current may flow to and from the sensor. The voltage potential is provided by an appropriate pulse generator 14.

The pulse generator 14 includes a connector assembly 16 to which the proximal end of a lead 18 may be detachably connected in conventional manner. The lead 18 includes a first conductor 20, represented schematically by a bold line, that connects a negative (−) terminal of the pulse generator 14 to a distal electrode 22. The conductor 20 is insulated by insulation 24', represented schematically by a narrow line on both sides of the bold line. The lead 18 also includes a second conductor 26 that connects a positive (+) terminal of the pulse generator to the positive (+) terminal of the sensor 12. A pin or feedthrough conductor 28 (hereafter "feedthrough pin 28"), is connected to the negative (−) terminal of the sensor 12 and passes through a suitable opening 30 of the insulation 24'. This feedthrough pin 28 is then electrically connected to the first conductor 20, e.g., by crimping, welding, or equivalent techniques. Additional insulation, not shown in FIG. 1 (and not relevant to the present discussion) may then be used to insulate the conductor 26 and exposed portions of the sensor 12.

The pulse generator 14 typically provides stimulation pulses at the tip electrode 22 by using the conductor 20 of the lead 19 unipolarly. That is, a negative pulse is generated by appropriate circuits within the pulse generator 14, and this pulse is coupled to the negative (−) terminal of the pacemaker connector 16. The pulse is then transferred to the distal electrode 22 via conductor 20. A return path is provided, in unipolar operation, through the conductive body fluids back to an appropriate exposed terminal on the housing of the pulse generator 14.

When operation of the sensor is desired, at times when a negative stimulation pulse is not present on the first conductor 20, a suitable voltage potential is applied between the first conductor 20 and the second conductor 26 of the lead 18. The signal path to the sensor 12 is thus provided from the positive (+) pulse generator terminal through the conductor 26 to the sensor positive (+) terminal. A return signal path is provided from the sensor negative (−) terminal, through the feedthrough pin 28 to the conductor 20, and through the conductor 20 back to the negative (−) pulse generator terminal.

Unfortunately, the process of passing the feedthrough pin 28 through the opening 30 of the insulation 24' compromises the integrity of the insulation at the point of feedthrough. Further, the process of connecting the feedthrough pin 28 to the conductor 20 at the feedthrough location comprises the integrity of the conductor 20. This is particularly the case over a long period of time when the lead 18 is subjected to a fluid environment and is further subjected to constant flexing and bending.

FIG. 2 is a schematic diagram illustrating the technique used by the present invention to overcome the problems associated with the use of an in-lead sensor as described above in FIG. 1. Like numerals are used to describe like parts in FIG. 2 (and the remaining figures) as were used in FIG. 1.

As seen in FIG. 2, an implantable lead/sensor 32 made in accordance with the present invention includes an integral sensor 12. The lead/sensor 32 includes a first conductor 20', represented schematically by a bold line, that connects a negative (−) terminal of a pulse generator 14, or similar medical device, to a distal electrode 22. The conductor 20' is insulated by insulation 24', represented schematically by a narrow line on both sides of the bold line. The lead/sensor 32 also includes a second conductor 26 that connects a positive (+) terminal of the pulse generator 14 to the positive (+) terminal of the sensor 12. A third conductor 27 connects a negative (−) terminal of the sensor 12 to the distal electrode 22. Additional insulation, not shown in FIG. 2 (and not relevant to the present discussion) may then be used to insulate the conductors 26 and 27, as well as exposed portions of the sensor 12.

The combined length of the conductor 26, the sensor 12, and the conductor 27 should be roughly equal to the length of the conductor 20'. As seen in FIG. 2, the sensor 12 is thus electrically connected in series with the conductors 26 and 27, and the respective lengths of the conductors 26 and 27 are selected to position the sensor 12 at a desired location along the length of the lead 32.

The lead 32 allows the pulse generator 14 to provide stimulation pulses at the tip electrode 22 by applying a negative pulse (using appropriate circuits within the pulse generator 14) to the negative (−) terminal of the pacemaker connector 16. The pulse is then transferred to the tip electrode 22 via conductor 20'. A return path is provided, in unipolar operation, through the conductive body fluids back to an appropriate exposed terminal on the housing of the pulse generator 14. Advantageously, there are no interruptions in the insulation 24' along the entire length of the lead/sensor 32. Nor are there any electrical connections made to the conductor 20' along the entire length of the lead/sensor 32. Thus, the conductor 20' provides a continuous, uninterrupted conductor/insulation route from the pulse generator 14 to the distal electrode 22, and long term impedance stability of the lead/sensor 32 in fluid environments is maintained.

When operation of the sensor is desired, at times when a negative stimulation pulse is not present on the first conductor 20', a suitable voltage potential is applied between the first conductor 20' and the second conductor 26 of the lead 32. The signal path to the sensor 12 is thus provided from the positive (+) pulse generator terminal through the conductor 26 to the sensor positive (+) terminal. A return signal path is provided from the sensor negative (−) terminal, through the third conductor 27 to the distal electrode 22, from the distal electrode 22 to the conductor 20', and through the conductor 20' back to the negative (−) pulse generator terminal.

In a preferred embodiment, the sensor 12 includes an LED and phototransistor, and is adapted to sense the presence of oxygen in blood by measuring the amount or radiation emitted by the LED that is reflected from the blood back to the phototransistor. The design and operation of such a sensor is described in U.S. Pat. No. 4,815,469. An alternative manner of designing and operating such a sensor is described in U.S. Pat. No. 5,040,538, issued 8/20/91, assigned to the same assignee as is the present application. The lead/sensor 32 of the present invention may advantageously be used with the sensor and operating method described in the '469 patent, the sensor and operating method described in the '208 application, or any other two-terminal sensor and operating method. Both the '469 patent and the '208 patent application are incorporated herein by reference.

As set forth in the referenced '469 patent or the '208 patent application, a preferred use of the lead/sensor 32 of the present invention is with a rate-responsive pacemaker. A rate-responsive pacemaker, as is known in the art, includes some sort of sensor that measures a physiological parameter (such as blood oxygen saturation) that indicates the physiological demands of the patient, and hence whether the rate at which the heart is paced by the pacemaker should increase or decrease. A rate-responsive pacemaker advantageously includes means for automatically adjusting the rate at which the heart is paced as a function of such measured physiological parameter. Hence, the lead/sensor 32 of the present invention is ideally suited for use with such a rate-responsive pacemaker because the pacing rate of the pacemaker may be automatically adjusted based on the sensed blood oxygen saturation (or other parameter) measured by the sensor 12.

When used with a rate-responsive pacemaker, it is generally preferred that the distal electrode 22 be positioned in a ventricle chamber of a mammalian heart, and the sensor 12 be positioned along the length of the lead/sensor 32 so as to reside in an atrial chamber of the heart. In this manner, the oxygen content of blood returned to the atrium can be monitored, and stimulation pulses can be delivered to the ventricle, as required. Other pacing/sensing configurations are, of course, also possible.

It should be emphasized, however, that the lead/sensor 32 of the present invention may be used for other applications besides rate responsive pacing. Any application requiring electrical contact with mammalian tissue and monitoring of a physiological parameter may find use of the present invention.

Figure 3B:
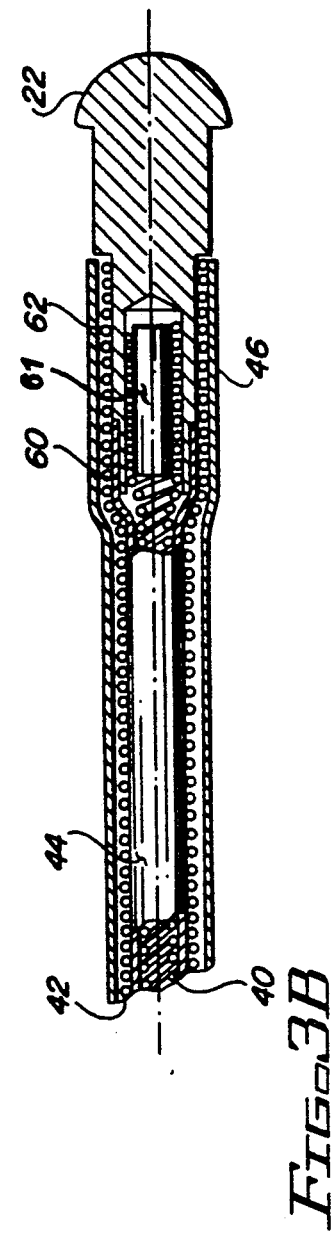

Advantageously, the present invention may be readily implemented using a conventional coaxial bipolar lead construction. Such construction is seen in FIGS. 3A and 3B. FIGS. 3A and 3B are sectional views, respectively, of a sensor portion and a distal electrode portion of an implantable lead with integral sensor made in accordance with the present invention. As seen in these figures, the basic lead construction includes a first helically wound conductor 40 positioned coaxially inside a second helically wound conductor 42. A layer of insulation 44 separates the first or inner conductor 40 from the second or outer conductor 42. Further, an insulating sheath 46 overlies the outer or second conductor 42. The method of manufacturing such bipolar coaxial leads is known in the art.

In accordance with the present invention, an in-lead sensor 12 is connected in series with the outer conductor 42 of a bipolar coaxial lead, while the inner conductor 40, including the insulation 44 overlying the inner conductor 40, passes through the sensor 12 uninterrupted. The outer conductor 42 is broken or separated into two portions, a proximal portion 50 and a distal portion 52. A first end 51 of the outer conductor 42 is secured to a positive terminal 54 of the sensor 12. Similarly, a second end 53 of the outer conductor 42 is secured to a negative terminal 56 of the sensor 12. As described below (in connection with FIG. 4), the sensor terminals 54 and 56 are preferably tubular in shape having a diameter slightly larger than the normal, non-stretched, diameter of the outer helically wound conductor 42. Securing the appropriate ends of the distal and proximal portions of the conductor 42 to the terminals 54 and 56 may thus be readily achieved by simply stretching the helically wound conductor 42 over the tubular terminals 54 and 56. The inherent spring force in the helically wound conductor holds the conductor 42 in tight physical, and hence electrical, contact with the tubular sensor terminals. Appropriate polyurethane tubing 58, and/or adhesive/potting material 59, is then placed over the interface between the conductor 42 and the sensor terminals 54 and 56, in order to electrically insulate this connection.

At the distal electrode 22, seen in FIG. 3B, both the inner conductor 40 and the outer conductor 42 are mechanically and electrically secured to the distal electrode 22. To facilitate this connection, the electrode 22 includes, at its proximal end, a first shoulder 60 having a diameter slightly larger than that of the inner conductor 40, and a second shoulder 62 having a diameter slightly larger than that of the outer conductor 42. The inner conductor 40 is stretched over a crimp tube 61. The intermediate insulating layer 44 is stretched over the shoulder 60 and secured with an appropriate polyurethane adhesive. Similarly, the outer conductor 42 is stretched over the shoulder 62. The outer insulating layer 46 is stretched over this stretched portion of the conductor 44 and secured with an appropriate adhesive.

Figure 4:
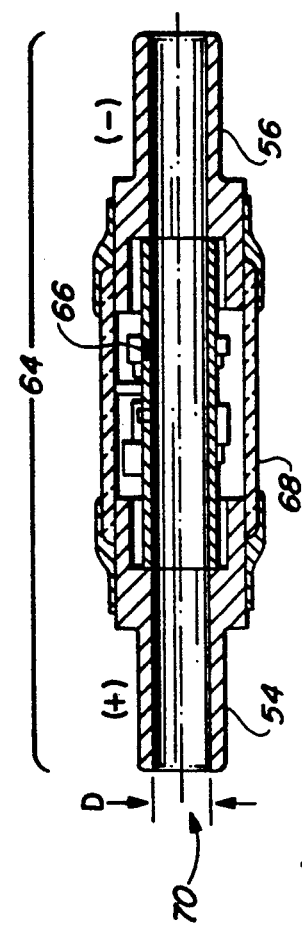
FIG. 4 is a sectional view of the sensor used with the lead and sensor combination shown in FIG. 3A.

Referring next to FIG. 4, a sectional view of the in-lead sensor 12 used with the lead/sensor 32 of the present invention is illustrated. The sensor 12 includes a sensor body 64 made up of the positive terminal 54, the negative terminal 56, a circuit tube 66, and a tube cover 68. The circuit tube 66, which may be made from any suitable non-conductor, such as a ceramic, and the tube cover 68, which is also made from a suitable non-conductive material, such as glass or quartz, mechanically bridge between the terminals 54 and 56. Further, appropriate electrical connection is made between various circuit components mounted on the circuit tube 66 and the terminals 54 and 56.

Conventional means, e.g., as described in the aforecited '469 patent, are used to mechanically and electrically secure these components together so as to form a rugged, sealed assembly.

Most significant for purposes of the present invention is that a lumen or tunnel 70 passes through the center of the sensor body 64. This tunnel 70 has a diameter D sufficiently large to allow the inner conductor 40, and its insulating layer 44, to pass therethrough uninterrupted. That is, no mechanical or electrical connections are made with the inner conductor 40, nor with its insulating layer 44, as it passes through the sensor body. This allows the inner conductor 40 to perform its intended function, e.g., delivering stimulation pulses to cardiac tissue, without any obstruction or interference from the circuits associated with the sensor 12. Further, the integrity of the conductor 40 and the insulation 44 is not compromised by the presence of the sensor 12. The sensor 12, however, advantageously utilizes the conductor 40 to provide a suitable signal path (via the distal electrode 22) when operation of the sensor is required.

As seen from the above description, the present invention thus provides an implantable lead that includes an implantable sensor as an integral part thereof. Advantageously, the sensor is fully operable from a proximal end of the lead, yet the sensor does not interfere in any way with use of the implantable lead.

As further seen from the above description, the present invention provides such an implantable lead/sensor combination that maximizes the insulation distance between electrical contacts of the lead. Hence, the lead provides long term impedance stability in fluid environments. Further, the described lead ensures a continuous, uninterrupted, uncontacted, conductor/insulation signal path from a proximal connector to a distal electrode.

As also seen from the above description, the present invention provides an implantable lead/sensor combination that utilizes a conventional two-conductor (bipolar) coaxial lead body assembly. Hence, the manufacture of the lead/sensor combination is greatly facilitated.

Finally, as further described above, in one embodiment the present invention provides a blood oxygen sensor as an integral part of an implantable pacemaker lead. The oxygen sensor is fully operable from a proximal end of the lead, yet it does not interfere in any way with the operation of the pacemaker lead. Thus, the lead/sensor combination is especially well suited for use with a rate responsive pacemaker to reliably measure the oxygen content of blood, which measurement is then used as a parameter to adjust the pacing rate of the pacemaker.

While the invention herein disclosed has been described by means of specific embodiments and applications thereof, numerous modifications and variations could be made thereto by those skilled in the art without departing from the scope of the invention set forth in the claims.

What is claimed is:

1. An implantable lead and sensor for use with a medical device comprising:
    a first conductor having a proximal end and a distal end;
    first insulation means for electrically insulating said first conductor without interruption along its entire length;
    a tip electrode electrically connected to the distal end of said first conductor;
    a second conductor having a proximal end and a distal end, the distal end being electrically connected to said tip electrode;
    a sensor having first and second terminals to which electrical contact must be made for operation of said sensor, said sensor being electrically inserted in series with said second conductor at a location intermediate the proximal and distal ends of said second conductor, the proximal end of said second conductor being electrically connected to said first sensor terminal, and the distal end of said second conductor being electrically connected to said second sensor terminal; and
    second insulation means for electrically insulating said second conductor along its entire length;
    said proximal ends of said first and second conductors being adapted for detachable electrical connection with said medical device;
    whereby electrical contact is continuously and uninterruptedly maintained with said tip electrode through said first conductor of said lead, thereby assuring impedance stability of said lead in fluid environments; and further
    whereby electrical contact may be selectively made with said sensor through the proximal end of said first conductor and the proximal end of said second conductor, the first terminal of said sensor being electrically contacted through the proximal end of said second conductor, and the second terminal of said sensor being electrically contacted through the proximal end of said first conductor by way of an electrical path through said first conductor to said tip electrode and through the distal end of said second conductor to said second sensor terminal.

2. The implantable lead and sensor as set forth in claim 1, wherein said first and second conductors comprise coaxial conductors; said first conductor comprising a first helically wound conductive wire, said first wound wire having a first diameter; said second conductor comprising a second helically wound conductive wire, said second wound wire having a second diameter; said first diameter being less than said second diameter so that said first conductor, including the first insulation means placed thereover, fits inside of the second wound wire.

3. The implantable lead and sensor as set forth in claim 2, wherein said sensor includes passage means therethrough for allowing said first conductor, including said first insulation means, to pass therethrough without interruption.

4. The implantable lead and sensor as set forth in claim 3, wherein said sensor comprises a physiological sensor adapted to sense a physiological parameter of mammalian tissue in which said lead and sensor are implanted.

5. The implantable lead and sensor as set forth in claim 4, wherein said physiological sensor comprises an oxygen sensor adapted to sense optically the oxygen content of blood in optical contact with said sensor.

6. The implantable lead and sensor as set forth in claim 3, wherein said lead comprises a pacemaker lead adapted for use with an implantable pacemaker, said tip electrode being adapted for insertion inside of a mammalian heart.

7. The implantable lead and sensor as set forth in claim 6, wherein said tip electrode is adapted for insertion into a ventricle chamber of said heart, and said sensor is spaced apart sufficiently far from said tip electrode along the length of said lead so as to not reside in said ventricle chamber.

8. The implantable lead and sensor as set forth in claim 7, wherein said sensor is spaced apart from said tip electrode along the length of said lead so as to reside in an atrial chamber of said heart.

9. An implantable lead and sensor combination comprising:
    a first conductor having a proximal end and a distal end;
    first insulation means for electrically insulating said first conductor without interruption along its entire length;
    a tip electrode electrically connected to the distal end of said first conductor;
    a second conductor having a proximal end and a distal end;
    a third conductor having a proximal end and a distal end, the distal end being electrically connected to said tip electrode;
    a sensor having first and second terminals to which electrical contact must be made for operation of said sensor, said sensor being electrically inserted in series with said second and third conductors, the distal end of said second conductor being connected to the first sensor terminal and the proximal end of the third conductor being connected to the second sensor terminal; and
    second insulation means for electrically insulating said second and third conductors along their entire length;

said proximal ends of said first and second conductors being adapted for detachable electrical connection with a medical device;

whereby electrical contact is continuously and uninterruptedly maintained with said tip electrode through said first conductor, thereby assuring impedance stability of said first conductor in fluid environments; and further whereby electrical contact may be selectively made with said sensor through the proximal end of said first conductor and the proximal end of said second conductor, the first terminal of said sensor being electrically contacted through the proximal end of said second conductor, and the second terminal of said sensor being electrically contacted through the proximal end of said first conductor by way of an electrical path through said first conductor to said tip electrode and through said third conductor to said second sensor terminal.

10. The implantable lead and sensor as set forth in claim 9, wherein said first, second and third conductors comprise coaxial conductors; said first conductor comprising a first helically wound conductive wire, said first wound wire a first diameter; said second and third conductors each comprising a second helically wound conductive wire, said second wound wire having a second diameter; said first diameter being less than said second diameter so that said first wound wire, including the first insulation means placed thereover, fits inside of the second wound wire of said second conductor and third conductors 11. The implantable lead and sensor as set forth in claim 10, wherein said sensor includes passage means therethrough for allowing said first conductor, including said first insulation means, to pass therethrough without interruption.

12. The implantable lead and sensor as set forth in claim 11, wherein said sensor comprises a physiological sensor adapted to sense a physiological parameter of mammalian tissue in which said lead and sensor are implanted.

13. The implantable lead and sensor as set forth in claim 12, wherein said physiological sensor comprises an oxygen sensor adapted to sense optically the oxygen content of blood in optical contact with said sensor.

14. The implantable lead and sensor as set forth in claim 11, wherein said lead comprises a pacemaker lead adapted for use with an implantable pacemaker, said tip electrode being adapted for insertion inside of a mammalian heart.

15. The implantable lead and sensor as set forth in claim 14, wherein said tip electrode is adapted for insertion into a ventricle chamber of said heart, and said sensor is spaced apart sufficiently far from said tip electrode along the length of said lead so as not reside in said ventricle chamber.

16. The implantable lead and sensor as set forth in claim 15, wherein said sensor is spaced apart from said tip electrode along the length of said lead so as to reside in an atrial chamber of said heart.

17. A method of forming an implantable lead having a physiological sensor as an integral part thereof, said sensor having first and second spaced apart terminals to which electrical contact must be made during its operation, said method comprising the steps of:
 (a) attaching a first end of a first conductor to a tip electrode, said first conductor having a first length;
 (b) insulating said first conductor along said first length without interruption;
 (c) attaching a first end of a second conductor to the first terminal of said sensor, said second conductor having a second length that is less than the first length of the first conductor;
 (d) insulating said second conductor, including the connection of said second end of said second conductor with said first sensor terminal, along said second length without interruption;
 (e) attaching a first end of a third conductor to the second terminal of said sensor, and a second end of said third conductor to said tip electrode, said third conductor having a third length, said second and third lengths, plus the spatial separation of said first and second terminals being approximately equal to said first length of said first conductor;
 (f) insulating said third conductor, including the connection of said first end of said third conductor with said second sensor terminal, along said third length without interruption; and
 (g) attaching a connector to the first end of said first conductor and the first end of said second conductor, said connector allowing detachable electrical connection to be made to a suitable medical device.

18. The lead forming method as set forth in claim 17, wherein said sensor includes a passage way therethrough, and wherein said method further includes inserting said first conductor, after being insulated along its entire length, through said passage way.

19. The lead forming method as set forth in claim 18, wherein said second and third conductors are formed by helically winding a conductive wire to a prescribed diameter, thereby forming a lumen through the center of said second and third conductors, and wherein said lead forming method further includes inserting said insulted first conductor through said lumen formed in said second and third conductors.

* * * * *

UNITED STATES PATENT AND TRADEMARK OFFICE
CERTIFICATE OF CORRECTION

PATENT NO. : 5,275,171
DATED : January 4, 1994
INVENTOR(S) : James E. Barcel

It is certified that error appears in the above-indentified patent and that said Letters Patent is hereby corrected as shown below:

In column 6, line 66, delete "'208 application" and substitute therefor --'538 patent--.

In column 6, lines 67-68, delete "'208 patent application" and substitute therefor --'538 patent--.

In column 7, lines 1-2, delete "'208 patent application" and substitute therefor --'538 patent--.

Signed and Sealed this

Ninth Day of April, 1996

*Attest:*

BRUCE LEHMAN

*Attesting Officer*     *Commissioner of Patents and Trademarks*